United States Patent
Harnett et al.

(10) Patent No.: US 6,887,891 B2
(45) Date of Patent: May 3, 2005

(54) DERIVATIVES OF LIPOIC ACID, THEIR PREPARATION, THEIR USE AS MEDICAMENTS AND THE PHARMACEUTICAL COMPOSITIONS CONTAINING THEM

(75) Inventors: Jeremiah Harnett, Gif-sur-Yvette (FR); Michel Auguet, Palaiseau (FR); Pierre-Etienne Chabrier de Lassauhyere, Paris (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 177 days.

(21) Appl. No.: 10/419,671

(22) Filed: Apr. 21, 2003

(65) Prior Publication Data

US 2004/0019084 A1 Jan. 29, 2004

Related U.S. Application Data

(62) Division of application No. 09/937,823, filed as application No. PCT/FR00/00814 on Mar. 31, 2000, now Pat. No. 6,605,637.

(30) Foreign Application Priority Data

Apr. 2, 1999 (FR) ............................................. 11-04132
Feb. 24, 2000 (FR) ......................................... 2000-02315

(51) Int. Cl.$^7$ ........................ A61K 31/44; C07D 409/60
(52) U.S. Cl. ..................................... 514/342; 546/280.4
(58) Field of Search ........................ 514/342; 546/280.4

(56) References Cited

U.S. PATENT DOCUMENTS

| | | | | |
|---|---|---|---|---|
| 6,313,164 B1 | * | 11/2001 | Fujita et al. | 514/440 |
| 6,331,559 B1 | * | 12/2001 | Bingham et al. | 514/440 |
| 6,369,098 B1 | * | 4/2002 | Pershadsingh et al. | 514/440 |
| 6,387,945 B2 | * | 5/2002 | Packer et al. | 514/440 |
| 6,492,405 B2 | * | 12/2002 | Haj-Yehia | 514/369 |

* cited by examiner

*Primary Examiner*—Deborah C. Lambkin
(74) *Attorney, Agent, or Firm*—Muserlian, Lucas and Mercanti

(57) ABSTRACT

Compounds of formula

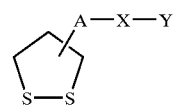

(Ia)

wherein the substituents are as defined in the specification which compounds are useful for inhibiting the activity of NO-synthase enzymes.

12 Claims, No Drawings

DERIVATIVES OF LIPOIC ACID, THEIR PREPARATION, THEIR USE AS MEDICAMENTS AND THE PHARMACEUTICAL COMPOSITIONS CONTAINING THEM

This application is a division of U.S. patent application Ser. No. 09/937,823 filed Sep. 27, 2001, now U.S. Pat. No. 6,605,637, which is a 371 of PCT/FR00/00814 filed Mar. 31, 2000.

A subject of the present invention is new derivatives of lipoic acid, which have an inhibitory activity on NO-synthase enzymes producing nitrogen monoxide NO and/or are agents which allow the regeneration of antioxidants or entities which trap the reactive oxygen species (ROS) and which intervene in a more general fashion in the redox status of thiol groups. These antioxidants or entities which trap the reactive oxygen species can be of natural origin, such as for example vitamin E or glutathione, or of synthetic origin such as certain products which trap the ROS or products having both an inhibitory activity on NO-synthase enzymes and an activity which traps the ROS. Examples of such products of synthetic origin can in particular be found in the PCT Patent Applications WO 96/09653, WO 98/42696 and WO 98/58934.

Therefore, the invention relates in particular to the derivatives corresponding to general formula (I) defined below, their preparation methods, the pharmaceutical preparations containing them and their use for therapeutic purposes, in particular their use as NO-synthase inhibitors and/or as agents which allow the regeneration of antioxidants or entities which trap the ROS's and which intervene in a more general fashion in the redox status of thiol groups.

Given the potential role of NO and the ROS's and the metabolism of glutathione in physiopathology, the new derivatives described corresponding to general formula (I) may produce beneficial or favourable effects in the treatment of pathologies where nitrogen monoxide and the metabolism of glutathione as well as the redox status of thiol groups are involved. In particular:

cardiovascular and cerebrovascular disorders including for example atherosclerosis, migraine, arterial hypertension, septic shock, ischemic or hemorragic cardiac or cerebral infarctions, ischemias and thromboses.

disorders of the central or peripheral nervous system such as for example neurodegenerative diseases where there can in particular be mentioned cerebral infarctions, sub-arachnoid haemorrhaging, ageing, senile dementias including Alzheimer's disease, Huntington's chorea, Parkinson's disease, Creutzfeld Jacob disease and prion diseases, amyotrophic lateral sclerosis but also pain, cerebral and bone marrow traumas, addiction to opiates, alcohol and addictive substances, erective and reproductive disorders, cognitive disorders, encephalopathies, encephalopathies of viral or toxic origin, depression, anxiety, schizophrenia, epilepsy, sleeping disorders, eating disorders (anorexia, bulimia etc.);

disorders of the skeletal muscle and neuromuscular joints (myopathy, myositis) as well as cutaneous diseases.

proliferative and inflammatory diseases such as for example atherosclerosis, pulmonary hypertension, respiratory distress, glomerulonephritis, cataracts, portal hypertension, psoriasis, arthrosis and rheumatoid arthritis, fibroses, amyloidoses, inflammations of the gastrointestinal system (colitis, Crohn's disease) or of the pulmonary system and airways (asthma, sinusitis, rhinitis) as well as contact or delayed hypersensitivities;

organ transplants.

auto-immune and viral diseases such as for example lupus, AIDS, parasitic and viral infections, diabetes and its complications including retinopathies, nephropathies and polyneuropathies, multiple sclerosis, myopathies;. cancer.

autosomal genetic diseases such as Unverricht-Lundborg disease;

neurological diseases associated with intoxications (Cadmium poisoning, inhalation of n-hexane, pesticides, herbicides), associated with treatments (radiotherapy) or disorders of genetic origin (Wilson's disease).

impotence linked to diabetes;

all the pathologies characterized by an excessive production or a dysfunction of nitrogen monoxide and/or the metabolism of glutathione and of the redox status of the thiol groups.

In all these pathologies, there is experimental evidence demonstrating the involvement of nitrogen monoxide or of a dysfunction of the metabolism of glutathione (Kerwin et al., Nitric oxide: a new paradigm for second messengers, *J. Med. Chem.* 38, 4343–4362, 1995; Packer et al., Alpha-lipoic acid as biological antioxidant, *Free Radical Biology & Medicine* 19, 227–250, 1995). This is the case in particular in Parkinson's disease which illustrates the invention (Beal MF, Excitotoxicity and nitric oxide in Parkinson's disease pathogenesis. *Ann. Neurol.* 44[Suppl 1], S110–S114, 1998; Donato et al., Gluthathione in Parkinson's disease: a link between oxidative stress and mitochondrial damage. *Ann. Neurol.* 32, S111–S115, 1992). In this context, medicaments which can inhibit the formation of nitrogen monoxide or re-establish the biological functionality of the thiol groups or glutathione can have beneficial effects.

Moreover, in earlier patents, the inventors have already described NO Synthase inhibitors and their use (U.S. Pat. Nos. 5,081,148; 5,360,925) and more recently the combination of these inhibitors with products having antioxidant or antiradicular properties (PCT Patent Application WO/09653). They have also described derivatives of amidines in PCT Patent Applications WO 98/42696 and WO 98/58934 and of the derivatives of aminopyridines in the PCT Patent Application WO 00/02860. These derivatives of amidines or aminopyridines have the characteristic of being both NO Synthase inhibitors and ROS inhibitors A subject of the present invention is new derivatives of lipoic acid, their preparation and their use in therapeutics.

Therefore the invention relates to a product of general formula (I), characterized in that it comprises the products of sub-formulae (I)a and (I)b

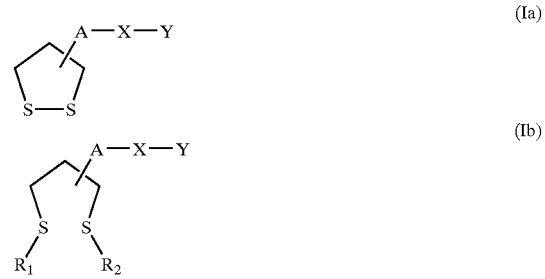

in which $R_1$ and $R_2$ represent independently a hydrogen atom or a linear or branched alkyl radical with 1 to 6 carbon atoms;

A represents one of the $-(CH_2)_m-NR_3CO(CH_2)_n-$, $-(CH_2)_m-CONR_3-(CH_2)_n-$, $-(CH_2)_m-NR_3$ —(CH$_2$)$_n$—, —(CH$_2$)$_m$—CONR$_3$—(CH$_2$)$_p$—NR$_4$—(CH$_2$)$_n$—, —(CH$_2$)$_m$—NR$_3$—CO—NR$_4$—CH$_2$)$_n$— or —(CH$_2$)$_m$— radicals, m and n being integers from 0 to 6, p being an integer from 2 to 6, and R$_3$ and R$_4$ representing independently a hydrogen atom or a linear or branched alkyl radical with 1 to 6 carbon atoms;

X represents a

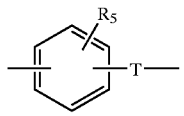

radical, in which the T group, which is attached to the Y group, represents a —(CH$_2$)$_i$— radical in which i represents an integer comprised between 0 and 6, and R$_5$ represents a hydrogen atom, a linear or branched alkyl radical having 1 to 6 carbon atoms or a —(CH$_2$)$_m$-Q radical in which Q represents a halogen atom or a hydroxy, cyan, amino, alkoxy, alkylthio, alkylamino or dialkylamino radical, or also R$_5$ represents a heterocycle with 5 to 6 members the heterocyclic members of which are chosen from the —O—, —N(R$_6$)— and —S— radicals, R$_6$ representing a hydrogen atom, a linear or branched alkyl having 1 to 6 carbon atoms or the bond to the phenyl ring of the X radical;

or also X represents a —(CH$_2$)$_q$— radical in which q represents an integer from 0 to 6;

and finally Y represents one of the

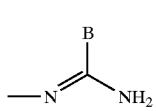 or 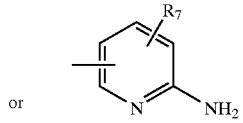

radicals in which:

B represents a linear or branched alkyl radical having 1 to 6 carbon atoms, carbocyclic or heterocyclic aryl with 5 or 6 members containing 1 to 4 heteroatoms chosen from O, S, N and in particular the thiophene, furane, pyrrole or thiazole radicals, the aryl radical being optionally substituted by one or more groups chosen from the linear or branched alkyl, alkenyl or alkoxy radicals having 1 to 6 carbon atoms, or B represents NR$_8$R$_9$, in which R$_8$ and R$_9$ represent, independently, a hydrogen atom or a linear or branched alkyl radical having 1 to 6 carbon atoms, or one of R$_8$ and R$_9$ represents a nitro radical while the other represents a hydrogen atom or a linear or branched alkyl radical having 1 to 6 carbon atoms, or also R$_8$ and R$_9$ together form with the nitrogen atom a non-aromatic heterocycle with five to six members, the elements of the chain being chosen from a group composed of —CH$_2$—, —NH—, —O— or —S—, or also B represents an SR$_{10}$ radical in which R$_{10}$ represents a hydrogen atom or a linear or branched alkyl radical having 1 to 6 carbon atoms, and R$_7$ represents a hydrogen atom or a linear or branched alkyl radical with 1 to 6 carbon atoms;

or a salt of a product of general formula (I).

Preferably, when R$_5$ represents a heterocycle with 5 to 6 members, R$_5$ will be one of the following heterocycles: pyrrole, imidazole, pyrazole, triazole, thiazolidine, pyrrolidine, piperidine, piperazine, N-alkyl-piperazine, thiomorpholine, morpholine, azetidine.

Moreover, the invention relates in particular to the products of general formula (I) defined previously, in which the following characteristics are found, independently:

A represents one of the —(CH$_2$)$_m$—NR$_3$CO—(CH$_2$)$_n$—, —(CH$_2$)$_m$—CONR$_3$—(CH$_2$)$_n$— or —(CH$_2$)$_m$—NR$_3$—CO—NR$_4$—(CH$_2$)$_n$ radicals m representing an integer from 0 to 4 and n an integer from 0 to 6, and R$_3$ and R$_4$ representing independently a hydrogen atom or a linear or branched alkyl radical with 1 to 6 carbon atoms;

X represents the

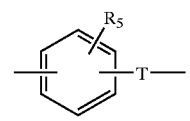

radical, in which the T group, which is attached to the Y group, represents a —(CH$_2$)$_i$— radical in which i represents 0 or 1, and R$_5$ represents a hydrogen atom, a linear or branched alkyl radical having 1 to 6 carbon atoms or a —(CH$_2$)$_m$-Q radical in which Q represents a halogen atom or a hydroxy, cyano, amino, alkoxy, alkylamino or dialkylamino radical, or R$_5$ represents a heterocycle with 5 to 6 members the heterocyclic members of which are chosen from the —O—, —N(R$_6$)— and —S— radicals, R$_6$ representing a hydrogen atom, a linear or branched alkyl having 1 to 6 carbon atoms or the bond to the phenyl ring of the X radical; or Y represents the

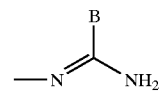

radical, in which B represents a linear or branched alkyl radical having 1 to 6 carbon atoms, a carbocyclic or heterocyclic aryl radical with 5 or 6 members containing 1 to 4 heteroatoms chosen from O, S, N and in particular the thiophene, furane, pyrrole or thiazole radicals, the aryl radical being optionally substituted by one or more groups chosen from the linear or branched alkyl, alkenyl or alkoxy radicals having 1 to 6 carbon atoms.

More particularly, the invention relates to the following products described in the examples (sometimes in the form of salts):

—N-{4-[[(2-thienyl)(imino)methyl]amino]phenyl}-1,2-dithiolane-3-pentanamide;

—N-{2-{4[[(2-thienyl)(imino)methyl]amino] phenyl}ethyl}-1,2-dithiolane-3-pentanamide;

—N-{2-{4[[(2-thienyl)(imino)methyl]amino] phenyl}ethyl}-1,2-dithiolane-3-acetamide;

—N-[4-(6-amino-4-methyl-2-pyridinyl)butyl]-1,2-dithiolane-3-pentanamide;

—N-[4-(6-amino-4-methyl-2-pyridinyl)butyl]-1,2-dithiolane-3-acetamide;

—N-(4-{[amino(2-thienyl)methylidene]amino}phenyl)-2-(1,2-dithiolan-3-yl)acetamide;

—N-(4-{[amino(2-thienyl)methylidene]amino}benzyl)-5-(1,2-dithiolan-3-yl)pentanamide;

—N-(5-{[amino(2-thienyl)methylidene]amino}-2-methoxyphenyl)-5-(1,2-dithiolan-3-yl)pentanamide;

—N-[5-{[amino(2-thienyl)methylidene]amino}-2-(dimethylamino)benzyl]-5-(1,2-dithiolan-3-yl) pentanamide;

—N-[5-{[amino(2-thienyl)methylidene]amino}-2-(1H-pyrrol-1-yl)benzyl]-5-(1,2-dithiolan-3-yl)pentanamide;

and the salts of these compounds.

Moreover, the invention offers a certain number of processes for accessing the products of general formula (I)

described above, processes the preferred conditions of which are described hereafter.

Therefore the invention relates in particular to a process for the preparation of an amidine of general formula (I) as defined previously, characterized in that the intermediate of general formula (II).

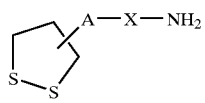

(II)

in which A and X are as defined above, is reacted with the intermediate of general formula (I.i).

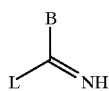

(I.i)

in which B is as defined above and L represents a parting group, for example an alkoxy, alkylthio, sulphonic acid, halide, aryl alcohol or tosyl radical.

Moreover, the invention relates to a process for the preparation of a compound of general formula (I) in which A represents a —(CH$_2$)$_m$—CONR$_3$—(CH$_2$)$_n$— radical as defined previously, characterized in that the intermediate of general formula (VII)a represented below HN(R$_3$)-A'-X—Y (VII)a R$_3$, X and Y being as defined above and A' representing the —(CH$_2$)$_n$— radical, n being as defined above, is reacted with the compound of general formula (I.vi)

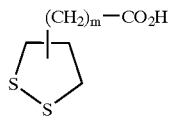

(I.vi)

m being as defined above.

Moreover, the invention relates to a process for the preparation of a compound of general formula (I) in which A represents a —(CH$_2$)$_m$—NR$_3$—CO—NR$_4$—(CH$_2$)$_n$ radical as defined previously, characterized in that the intermediate of general formula (VII)b represented below HN(R$_4$)-A'-X—Y (VII)b R$_4$, X and Y being as defined above and A' representing the —(CH$_2$)$_n$— radical, n being as defined above, is reacted with the compound of general formula (I.vi)

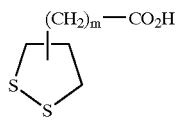

(I.vi)

m being as defined above, and with diphenylphosphorylazide in the presence of a base such as for example triethylamine.

The invention also relates to a process for the preparation of a compound of general formula (I) in which B is an amine, characterized in that the intermediate of general formula (II)

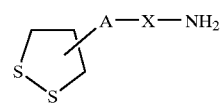

(II)

in which A and X are as defined above is reacted,
a) with the intermediate of general formula (I.ii)

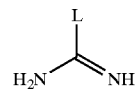

(I.ii)

in which L represents a parting group, for example an alkoxy, alkylthio, sulphonic acid, halide, aryl alcohol or tosyl radical,
b) or with the intermediate of general formula (I.iii)

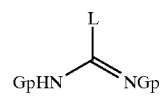

(I.iii)

in which L represents a parting group, for example an alkoxy, alkylthio, sulphonic acid, halide, aryl alcohol or tosyl radical, and Gp a protective group of carbamate type, for example the t-butoxycarbonyl group, this reaction being followed, in the case where reaction with a compound of general formula (I.iii) is chosen, by hydrolysis in the presence of a strong acid, for example trifluoroacetic acid, c) or with the derivative of formula (I.iv) (N-methyl-N'-nitro-N-nitrosoguanidine)

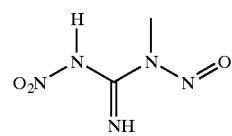

(I.iv)

d) or finally with the derivative of formula (I.v) in which Gp represents a protective group S=.=N-Gp (I.v)

In certain cases, the compounds according to the present invention can comprise asymmetrical carbon atoms, and therefore have two possible enantiomeric forms, i.e. "R" and "S" configurations. The present invention includes the two enantiomeric forms and all combinations of these forms, including the racemic "RS" mixtures. In an effort to simplify matters, when no specific configuration is indicated in the structural formulae, it should be understood that the two enantiomeric forms and their mixtures are represented.

Moreover, in the present application, unless otherwise specified, by alkyl is meant a linear or branched alkyl radical comprising 1 to 6 carbon atoms. By alkenyl, unless otherwise specified, is understood a linear or branched alkyl radical comprising 1 to 6 carbon atoms and having at least one unsaturation (double bond).

By alkylthio, alkoxy, alkylamino, dialkylamino and alkenyl radicals are meant the alkylthio, alkoxy, alkylamino, dialkylamino and alkenyl radicals respectively the alkyl radical of which has the meaning indicated previously.

By linear or branched alkyl radical having 1 to 6 carbon atoms is meant in particular the methyl, ethyl, propryl, isopropyl, butyl, isobutyl, sec-butyl and tert-butyl, pentyl, neopentyl, isopentyl, hexyl, isohexyl radicals. By halogen is meant the fluorine, chlorine, bromine or iodine atoms.

A subject of the invention is also, as medicaments, the compounds described previously or their pharmaceutically acceptable salts. It also relates to pharmaceutical compositions containing these compounds or their pharmaceutically acceptable salts, and the use of these compounds or of their pharmaceutically acceptable salts for producing medicaments intended to inhibit neuronal NO synthase or inductible NO synthase, to regenerate antioxidants which can be natural or synthetic, or to provide the double function of NO synthase inhibition and the regeneration of antioxidants.

By pharmaceutically acceptable salt is meant in particular addition salts of inorganic acids such as hydrochloride, hydrobromide, hydroiodide, sulphate, phosphate, diphosphate and nitrate, or of organic acids, such as acetate, maleate, fumarate, tartrate, succinate, citrate, lactate, methanesulphonate, p-toluenesulphonate, pamoate, oxalate and stearate. The salts formed from bases such as sodium or potassium hydroxide also fall within the scope of the present invention, when they can be used. For other examples of pharmaceutically acceptable salts, reference can be made to "Pharmaceutical salts", *J. Pharm. Sci.* 66:1 (1977).

A subject of the invention is also the use of a product of general formula (I) or of a pharmaceutically acceptable salt of this product in order to produce a medicament intended to treat pathologies in which nitrogen monoxide and/or the redox status of thiol groups are involved, pathologies such as disorders of the central or peripheral nervous system particularly well represented by Parkinson's disease, cerebrovascular disorders, proliferative and inflammatory diseases, vomiting, septic shock, pathologies resulting from radioactive irradiations, solar radiations or organ transplants, autoimmune and autosomal diseases, cancer and all the pathologies characterized by a production or a dysfunction involving nitrogen monoxide and/or involving the redox status of thiol groups.

A subject of the invention is also the use of a product of general formula (I) or of a pharmaceutically acceptable salt of this product, in order to produce a medicament intended to treat cerebrovascular disorders such as migraine, cerebral infarctions of ischemic or hemorragic origin, ischemias and thromboses.

Finally a subject of the invention is the use of a product of general formula (I) or of a pharmaceutically acceptable salt of this product in order to produce a medicament intended to treat disorders of the central or peripheral nervous system such as neurodegenerative diseases, pain, cerebral and bone marrow traumas, addiction to opiates, alcohol and addictive substances, erective and reproductive disorders, cognitive disorders, encephalopathies, depression, anxiety, schizophrenia, epilepsy, sleeping disorders and eating disorders.

The pharmaceutical compositions can be in the form of a solid, for example powders, granules, tablets, capsules, liposomes or suppositories. Appropriate solid supports can be for example calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in the form of a liquid, for example, solutions, emulsions, suspensions or syrups. Appropriate liquid supports can be, for example, water, organic solvents such as glycerol or glycols, as well as their mixtures, in varying proportions, in water.

A medicament according to the invention can be administered by topical, oral or parenteral route, by intramuscular injection, etc.

The envisaged administration dose for a medicament according to the invention is comprised between 0.1 mg and 10 g according to the type of active compound used.

In accordance with the invention, the compounds of general formula (I) can be prepared by the process described below.

PREPARATION OF THE COMPOUNDS OF GENERAL FORMULA (I)

A) Preparation of the Compounds of General Formula (I) where Y Represents

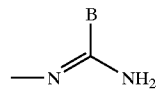

First Approach:

The compounds of general formula (I) can be prepared from the intermediates of general formula (II), (III) and (IV) according to Diagram 1 where A, B, X and Y, are as defined above and Gp is a protective group of carbamate type.

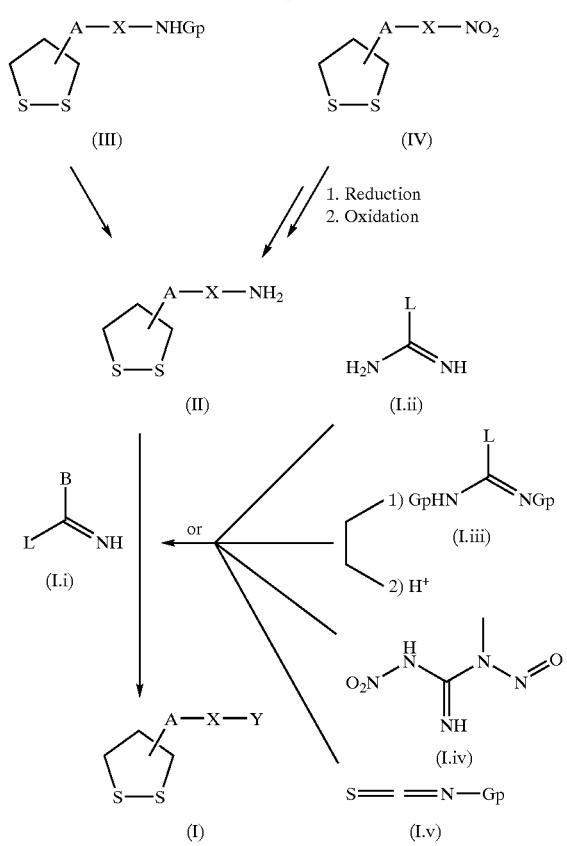

The aniline and amine derivatives of general formula (II), can be condensed with the compounds of general formula (I.i), in which L represents a parting group (in particular an alkoxy, alkylthio, sulphonic acid, halide, aryl alcohol or tosyl radical), in order to produce the final compounds of general formula (I) of substituted amidine type (cf. Diagram 1). For example, for B=thiophene, the derivatives of general formula (II) can be condensed with S-methylthiophene thiocarboxamide hydroiodide, prepared according to a method in the literature (*Ann. Chim.* (1962), 7, 303–337). The condensation can be carried out by heating in an alcohol (for example in methanol or isopropanol), optionally in the presence of DMF at a temperature preferably comprised between 50 and 100° C. for a duration generally comprised between a few hours and overnight.

In the case where B=SR$_{10}$, for example S—CH$_3$, this can be prepared by the condensation of the amines or anilines of general formula (II) with the isothiocyanate (I.v) in which Gp represents a protective group such as for example the benzoyl group. Then deprotection is carried out by cleavage of the protective group under appropriate conditions and the thiourea formed is finally treated with, for example, a halogeno-alkane in order to produce the final compounds of general formula (I).

In the case where B=NR$_8$R$_9$, the final compounds of general formula (I) are guanidines. These can be prepared, for example, by the condensation of the amines or anilines of general formula (II) with the derivatives of general formula (I.ii) or (I.iii). The reagents of general formula (I.ii) in which L represents, for example, a pyrazole ring are condensed with the amines of general formula (II) according to the conditions described in the literature (*J. Org. Chem.* (1992) 57, 2497–2502) similarly for the reagents of general formula (I.iii) in which L represents, for example, a pyrazole ring and Gp the tBuOCO group (*Tetrahedron Lett.* (1993) 34 (21), 3389–3392) or when L represents the —N—SO$_2$—CF$_3$ group and Gp the tBuOCO group (*J. Org. Chem.* (1998) 63, 3804–3805). During the final stage of the synthesis, deprotection of the guanidine function is carried out in the presence of a strong acid such as for example trifluoroacetic acid.

In the case where B=—NHNO$_2$ the final compounds of general formula (I) can be prepared, for example, by the condensation of the amines or anilines of general formula (II) with the reagent of formula (I.iv) (N-methyl-N'-nitro-N-nitrosoguanidine) according to the conditions described in the literature.(*J. Amer. Chem. Soc.* (1947), 69, 3028–3030).

The compounds of general formula (I)b, are obtained from the compounds of general formula (I)a where A, X and Y are as defined above. The conversion of the lipoic compounds of general formula (I)a to dihydrolipoic derivatives of general formula (I)b in which R$_1$=R$_2$=H is carried out in an alcoholic solvent such as, for example, methanol in the presence of a reducing agent such as for example NaB$_4$, NaBH$_3$CN or LiAlH$_4$. The compounds of general formula (I)b for which R$_1$ and R$_2$ are not H are prepared by reacting the compounds of general formula (I)b in which R$_1$=R$_2$=H with a compound of formula R$_1$-Hal and/or R$_2$-Hal (Hal= halogen atom) where R$_1$ and R$_2$ are as defined above and the halogen atom is a parting group. The reaction is carried out, for example, in an appropriate solvent such as THF, acetone, ethyl acetate in the presence of a base such as K$_2$CO$_3$ or triethylamine, in order to produce the intermediates of general formula (I)b.

Preparation of the Compounds of General Formula (II)

The intermediates of general formula (II), are obtained from the cleavage of a protective group (Gp) or by reduction of a nitro group.

The intermediates of general formula (II), in which A and X are as defined above, can be prepared from the intermediates of general formula (III) or (IV), Diagram 1, which are compounds containing respectively a protected amine or aniline (NHGp) in the form, for example, of a carbamate or a nitro group. In the particular case of the BOC groups, these are deprotected in a standard fashion using TFA or HCl, in order to finally produce the primary amines and anilines of general formula (II). The reduction of the nitro function of the intermediates of general formula (IV), Diagram 1, in which A, and X are as defined above, is carried out, for example, by heating the product in an appropriate solvent such as ethyl acetate with a little ethanol in the presence of SnCl$_2$ (*J. Heterocyclic Chem.* (1987), 24, 927–930; *Tetrahedron Letters* (1984), 25 (8), 839–842) in the presence of SnCl$_2$/Zn (*Synthesis.* (1996), 9,1076–1078), using NaBH$_4$—BiCl$_3$ (*Synth. Com.* (1995) 25 (23), 3799–3803) in a solvent such as ethanol, or then by using Raney Ni with hydrazine hydrate added to it (*Monatshefte für Chemie,* (1995), 126, 725–732), or using indium in an ethanol and ammonium chloride mixture under reflux (*Synlett* (1998) 9, 1028). Then, the double reduction product is reoxidized in the presence of ferric chloride (FeCl$_3$) (*Synlett* (1991) 10, 717–718 ) or iodine (*Tetrahedron Letters.*(1997), 38 (33), 5785–5788 ) in order to finally produce the amines and anilines again containing the dithiolane of general formula (II).

Preparation of the Compounds of General Formula (III) and (IV):

Synthesis of the Carboxamides of General Formula (III) and (IV):

The carboxamides of general formula (III) and (IV), Diagram 2, in which A, X, R$_3$ and m are as defined above, are prepared by condensation of the acids of general formula (I.vi) with the mono-protected amines or anilines of general formula (V) or the nitro derivatives of general formula (VI) in which A' represents the —(CH$_2$)$_n$— radical. The R$_x$ radical, in the synthesis diagrams of the present Application, signifies, depending on the case, R$_3$ or R$_4$. The carboxamides bonds are formed under the standard conditions of peptide synthesis (M. Bodanszky and A. Bodanszky, *The Practice of Peptide Synthesis,* 145 (Springer-Verlag, 1984)) in THF, dichloromethane or DMF in the presence of a coupling reagent such as dicyclohexylcarbodiimide (DCC), 1,1'-carbonyldiimidazole (CDI) (*J. Med. Chem.* (1992), 35 (23), 4464–4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)) or in the presence of isobutyl chloroformate and N-methylmorpholine (*Org. Prep. Proced. Int.,* (1975), 35, 215). The syntheses of the carboxylic acids of general formula (I.vi) and the amines/anilines of general formula (V) and (VI), which are not commercially available, are described hereafter.

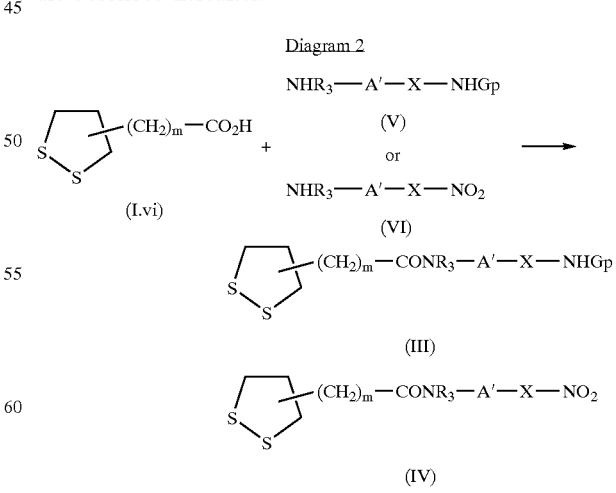

Diagram 2

Second Approach

The compounds of general formula (I) can also be prepared from the intermediates of general formula (VII), (VIIII), (IX) and (X) according to Diagram 3 in which A, B, X and Y are as defined above, A' represents the —(CH$_2$)$_n$— radical, the R$_x$ radical signifies, depending on the case, R$_3$ or R$_4$. and Gp is a protective group, for example a protective group of carbamate type.

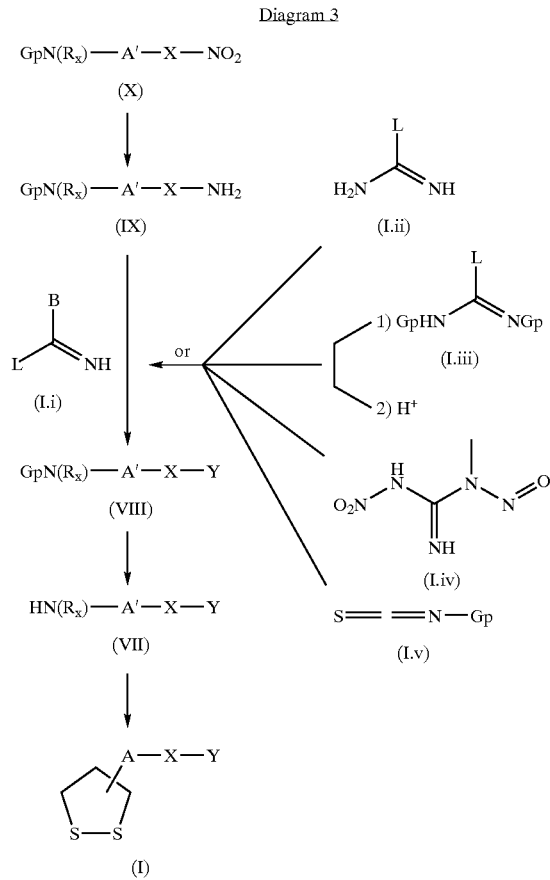

Synthesis of the Carboxamides of General Formula (I)

The carboxamides of general formula (I), Diagram 4, in which A', X, R$_3$, Y and m are as defined above, are prepared by condensation of the acids of general formula (I.vi) with the amines/anilines of general formula (VII). The carboxamide bonds are formed under standard conditions of peptide synthesis (M. Bodanszky and A. Bodanszky, *The Practice of Peptide Synthesis*, 145 (Springer-Verlag, 1984)) in THF, dichloromethane or DMF in the presence of a coupling reagent such as dicyclohexylcarbodiimide (DCC), 1,1'-carbonyldiimidazole (CDI) (*J. Med. Chem.* (1992), 35 (23), 4464–4472) or 1-(3-dimethylaminopropyl)-3-ethylcarbodiimide hydrochloride (EDC or WSCI) (John Jones, *The chemical synthesis of peptides*, 54 (Clarendon Press, Oxford, 1991)) or in the presence of isobutyl chloroformate and N-methylmorpholine (*Org. Prep. Proced. Int.*, (1975), 35, 215). The syntheses of the carboxylic acids of general formula (I.vi) which are not commercially available are described hereafter.

Diagram 4

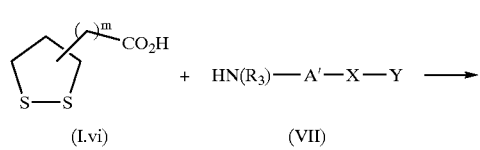
  + HN(R$_3$)—A'—X—Y ⟶
(I.vi)                    (VII)

-continued

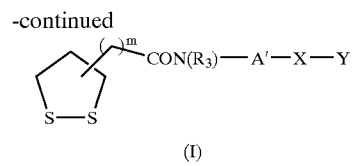

(I)

Synthesis of the Ureas of General Formula (I)

The ureas of general formula (I), Diagram 5, in which m, A', R$_4$, X and Y are as defined above, are prepared by condensation of the acids of general formula (I.vi) with the amines/anilines of general formula (VII) in a solvent such as toluene in the presence of diphenylphosphorylazide (DPPA) and a base such as for example triethylamine, preferably for 2 to 3 hours and by heating, preferably at a temperature of 40 to 110° C., for example at a temperature of 80° C.

Diagram 5

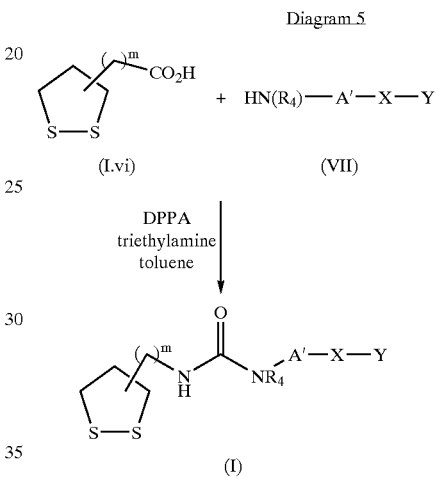

Preparation of the Compounds of General Formula (VII), (VIII), (IX) and (X):

The compounds of general formula (VII), are obtained by cleavage of a protective group. The compounds of general formula (VII), in which R$_x$, A', X and Y are as defined above, can be prepared from the compounds of general formula (VIII), Diagram 3, which are compounds containing a protected amine (NGp) in the form, for example, of a carbamate. In the particular case of the BOC groups, these are deprotected in a standard fashion using trifluoroacetic acid (TFA) or HCl, in order to finally produce the amines of general formula (VII).

The compounds of general formula (VIII) can be prepared from the intermediates of general formula (IX) and (X) according to Diagram 3 where B, A', X, Y and R$_x$ are as defined above and Gp is a protective group, for example of carbamate type.

The aniline/amine derivatives of general formula (IX) can be condensed with the compounds of general formula (I.i), (I.ii), and (I.iii), in which L represents a parting group, or the compounds of general formula (I.iv) and (I.v), as previously described for the compounds of general formula (I) in Diagram 1, in order to finally produce the compounds of general formula (VIII), Diagram 3. In the case where R$_3$ represents the 2-hydroxy-4,6-dimethoxybenzyl radical and Gp represents t-butoxycarbonyl (BOC), these conditions give rise to N-debenzylation in situ, in order to directly produce the compounds of general formula (VIII), Diagram 6.

Diagram 6

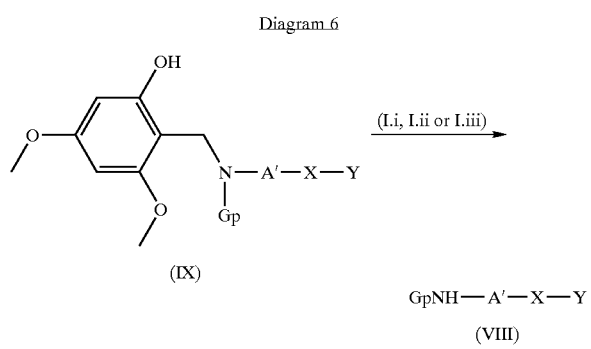

The compounds of general formula (IX), are obtained from the reduction of a nitro group of the compounds of general formula (X). The reduction of the nitro function of the compounds of general formula (X), Diagram 3, in which $R_x$, A' and X are as defined above, is carried out, for example, by heating the product in an appropriate solvent such as ethyl acetate with a little ethanol in the presence of $SnCl_2$ (*J. Heterocyclic Chem.* (1987), 24, 927–930; *Tetrahedron Letters* (1984), 25 (8), 839–842) in the presence of $SnCl_2/Zn$ (*Synthesis.* (1996), 9, 1076–1078) or using $NaBH_4$-$BiCl_3$ (*Synth. Com.* (1995) 25 (23), 3799–3803) in a solvent such as ethanol, or then by using Raney Ni with hydrazine hydrate added to it (*Monatshefte für Chemie,* (1995), 126, 725–732), or also using indium in a mixture of ethanol and ammonium chloride under reflux (*Synlett* (1998) 9, 1028), in order to finally produce the primary amines and anilines of general formula (IX).

The preparation of the compounds of general formula (X) which are not commercially available is described hereafter.

B) Preparation of the Compounds of General Formula (I) where Y Represents:

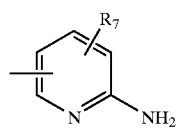

The compounds of general formula (I) in which A, X, Y and $R_7$ are as defined above, can be prepared from the intermediates of general formula (I) according to the procedure illustrated in Diagram 7.

Diagram 7

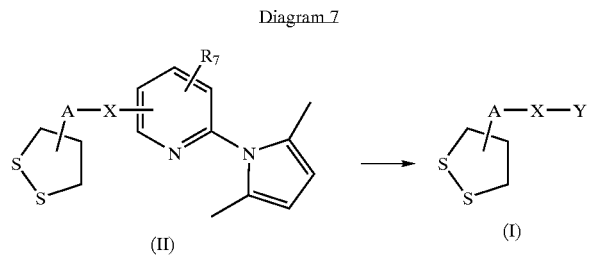

The final molecules of general formula (I) are obtained after cleavage of the 2,5-dimethylpyrrole protective group of the compounds of general formula (II) by heating in the presence of hydroxylamine hydrochloride, at a temperature which varies from 60° C. to 100° C., in a solvent such as for example ethanol according to an experimental protocol described in *J. Chem. Soc. Perkin Trans.* (1984), 12, 2801–2807.

Preparation of the Compounds of General Formula (II):

The compounds of general formula (II) can be prepared according to the following synthesis diagrams:

1) Methods of Accessing Substituted 2-(2,5-dimethylpyrrol-1-yl)pyridine of General Formula (II.x):

1.1) The synthetic precursors which lead to the intermediates of general formula (II) are prepared, Diagram 8, from the compounds of general formula (II.1), such as for example 2-(2,5-dimethylpyrrol-1-yl)-4,6-dimethylpyridine. This is obtained from commercial 6-amino-2,4-lutidine according to a experimental protocol described in *J. Chem. Soc. Perkin Trans.*, (1984), 12, 2801–2807. Treatment of the compounds of general formula (II.1) with a strong base such as, for example, n-BuLi, at a temperature which varies from –50° C. to –30° C. in an anhydrous solvent such as ethyl ether, under an inert atmosphere and optionally in the presence of N,N,N',N'-tetramethylethylenediamine allows the lithiated derivative to form (intermediate (II.2)) which in the presence of an electrophile E⁺ leads to the adducts of general formula (II.x).

Diagram 8

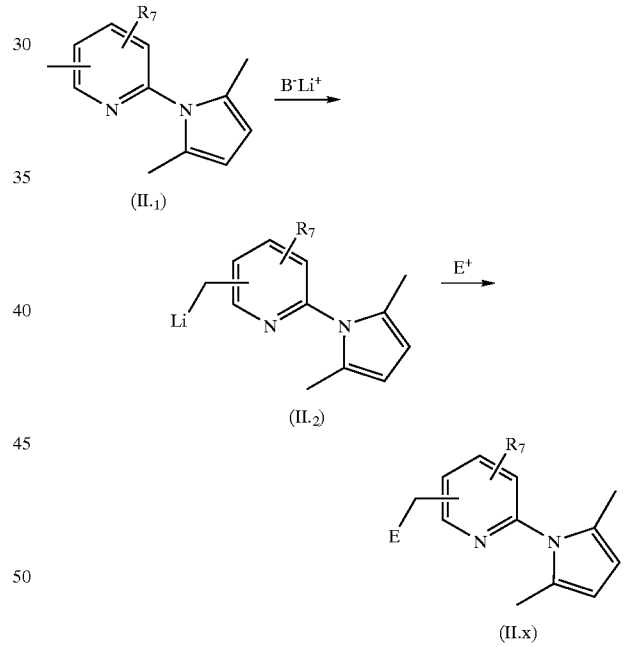

1.2) Among the electrophiles E⁺ which can react with the lithiated types of general formula (II.2), the protected halogeno-amines are for example found. The amines of general formula (II.3) are prepared from intermediate (II.2) which is condensed, for example, on protected halogeno-amines (for example in the form of silylated derivatives or phthalimides) under conditions which have been described previously. The amines of general formula (II.4) are finally obtained after deprotection under conditions described in the literature (T. W. Greene and P. G. M. Wuts, Protective Groups in Organic Synthesis, Second edition (Wiley-Interscience, 1991)).

Diagram 9

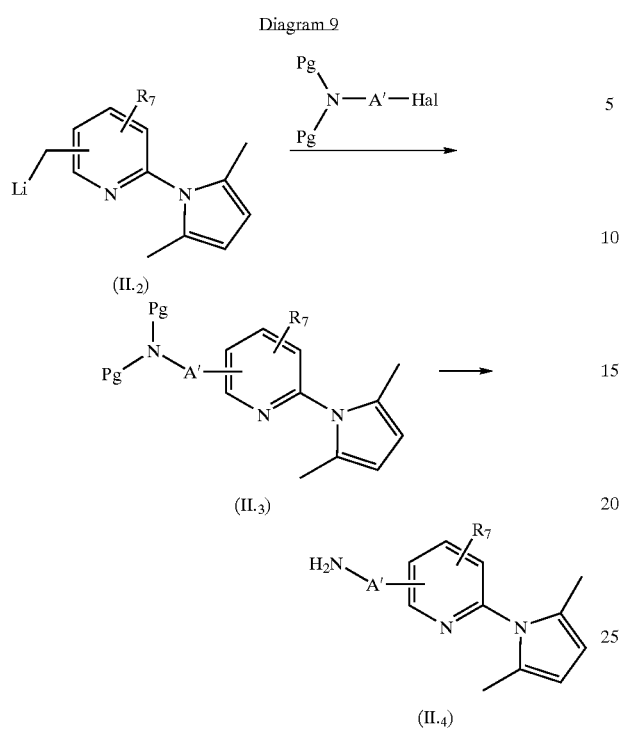

2) Methods of Accessing the Compounds of General Formula (II):

Preparation of the Carboxamides of General Formula (II):

The carboxamides of general formula (II), in which m, $R_3$, A' and $R_7$ are as defined above, can also be prepared, Diagram 10, by condensation of the carboxylic acids of general formula (I.vi) with the amines of general formula (II.4) under conditions which have been described previously. Synthesis of the carboxylic acids of general formula (I.vi), which are not commercially available, is described hereafter.

Diagram 10

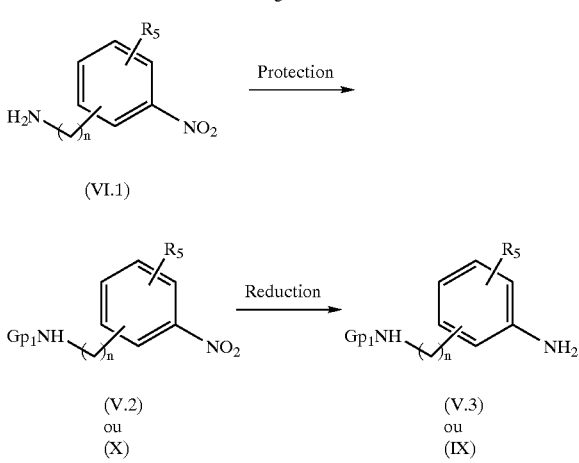

3) Preparation of Certain Non Commercial Synthetic Intermediates:

The acids of general formula (I.vi) which are not commercially available, in which m is as defined above are accessible via methods described in the literature. For example, trisnorlipoic acid is obtained in 5 stages according to an experimental protocol described in *Tetrahedron Letters* (1997), 38 (33), 5785–5788.

When X represents a —$(CH_2)_q$— radical, the selectively mono-protected primary amines of general formula (V) and (IX) in which $R_3$ represents H are accessible via methods described in the literature, (for example: *Synthesis* (1984), 12, 1032–1033; *Synth. Commun.* (1990), 20(16), 2559–2564; *J. Amer. Chem. Soc.* (1993), 115(9), 3548–3557; *J. Med. Chem.* (1989), 32(2), 391–396). *J. Amer. Chem. Soc.* (1995), 117(11), 3308–3309). The primary nitro-amines of general formula (VI) in which $R_3$ represents H are accessible via methods described in the literature (for example: *J. Chem. Soc.* (1947), 1487).

When X represents a phenylene radical and n and $R_5$ are as defined above, the amines/anilines of general formula (V) in which $R_3$ represents H are accessible via methods illustrated in Diagram 2.1 hereafter.

Diagram 2.1

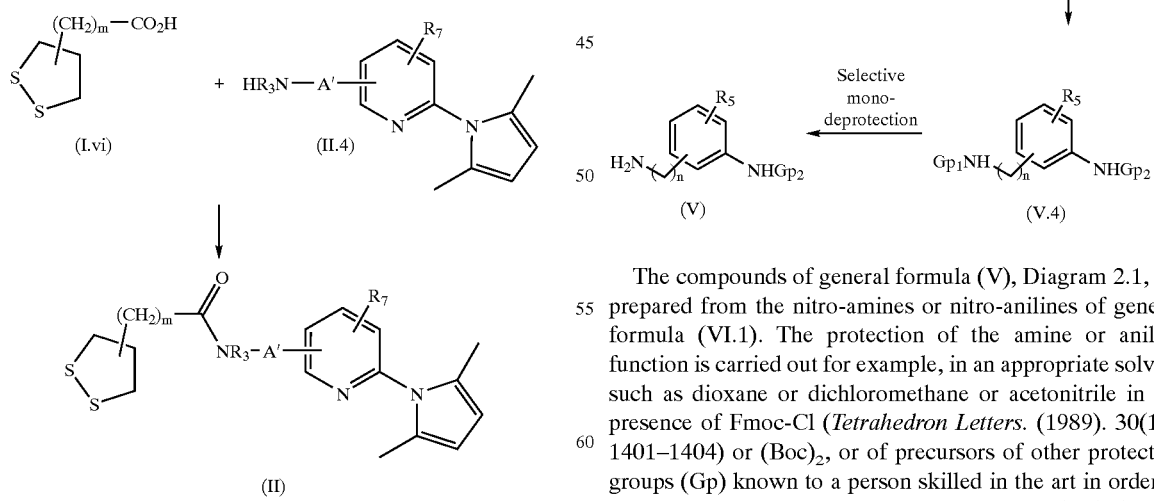

The compounds of general formula (V), Diagram 2.1, are prepared from the nitro-amines or nitro-anilines of general formula (VI.1). The protection of the amine or aniline function is carried out for example, in an appropriate solvent such as dioxane or dichloromethane or acetonitrile in the presence of Fmoc-Cl (*Tetrahedron Letters*. (1989). 30(11), 1401–1404) or $(Boc)_2$, or of precursors of other protective groups (Gp) known to a person skilled in the art in order to produce the compounds of general formula (V.2) (or the compounds of general formula (X)). The reduction of the nitro function of the intermediates of general formula (V.2) is generally carried out by catalytic hydrogenation, in ethanol, in the presence of 10% Pd/C or by other methods described previously, in order to produce the anilines (V.3) (or the compounds of general formula (IX)). Protection of the aniline function of general formula (V.3) is carried out, for example, in the presence of Fmoc-Cl or (Boc)$_2$ or of precursors of other protective groups (Gp) known to a person skilled in the art, it being understood that Gp$_1 \neq$Gp$_2$, Diagram 2.1. The last stage of the synthesis consists of regenerating the primary amine by mono-deprotection, for example, when Gp$_1$=Fmoc, the deprotection is carried out, for example, in an appropriate solvent such as DMF or dioxane, in the presence of a base such as piperidine, morpholine, DMAP, or diisopropylethylamine (*Tetrahedron Letters.* (1989), 30 (11), 1401–1404). When Gp$_2$=Boc, these are deprotected in a standard fashion using trifluoroacetic acid or HCl, in order to finally produce the mono-protected anilines of general formula (V).

The compounds of general formula (IX) and (X) for which R$_3$ represents the 2-hydroxy-4,6-dimethoxyphenol radical, Gp represents the Boc group and n and R$_5$ are as defined above, are prepared from the nitro-amines or nitro-anilines of general formula (VI.1), Diagram 6.1.

out by catalytic hydrogenation, in ethanol, in the presence of 10% Pd/C in order to produce the anilines (IX).

When X represents a phenylene radical and R$_5$ represents a heterocycle with 5 to 6 members comprising a nitrogen atom (het) or a group comprising a heteroatom W (group referred to as Wαβ where W=O, N or S, α representing alkyl and β not existing when W=O or S or β representing H or alkyl when W=N), Diagrams 3.1 and 3.2, the amines/anilines of general formula (X) which are not commercially available in which R$_3$ represents H are accessible via methods described in the literature (for example: *J. Med. Chem.* (1980), 23, 973–975; *J. Med. Chem.* (1990), 33, 633–641; *Chem. Heterocycl. Compd.* (EN). (1969), 5, 683–687; *J. Org. Chem. USSR.* (EN) (1989), 3, 599–600; *J. Med. Chem.* (1994), 37, 467–475; *J. Med. Chem.* (1999), 42, 4362–4379). For example, the compounds of general formula (X) can be prepared by the methods illustrated in Diagram 3.1.

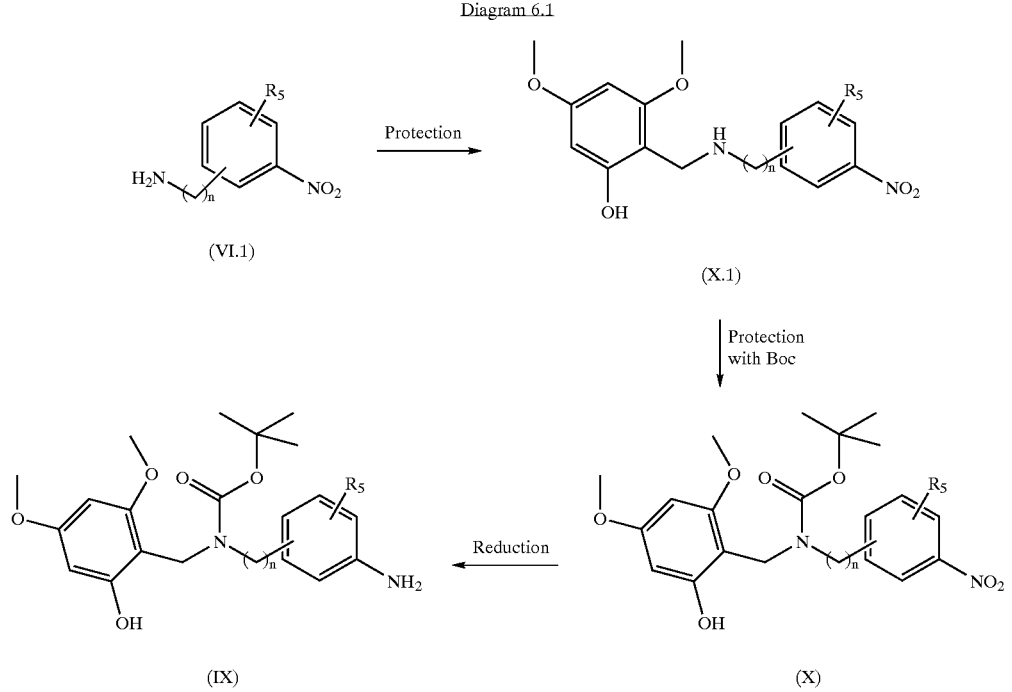

The compounds of general formula (IX) and (X) are prepared, Diagram 6.1, by condensation of 2-hydroxy-4,6-dimethoxybenzaldehyde with an amine/aniline of general formula (VI.1) in a reducing medium. The reaction takes place in an alcoholic solvent such as, for example, methanol, in the presence of a reducing agent such as, for example, NaBH$_4$ or NaBH$_3$CN. The protection of the secondary amine formed is then carried out in a standard fashion with (Boc)$_2$ in dichloromethane in order to produce the compounds of general formula (X). The reduction of the nitro function of the compounds of general formula (X) is carried

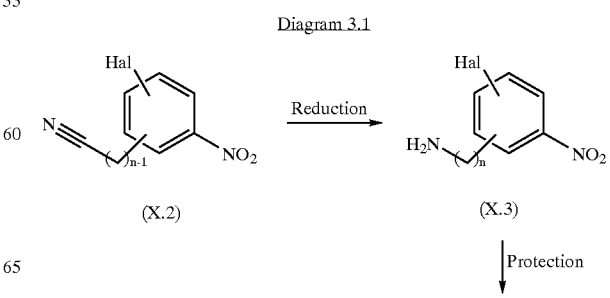

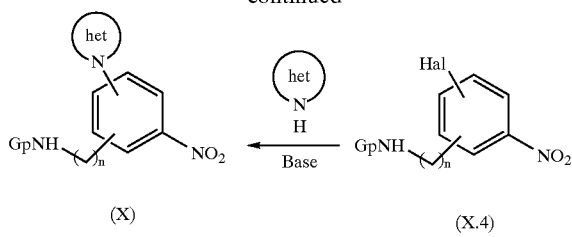

The compounds of general formula (X), Diagram 3.1, in which n, het and Wαβ are as defined above are prepared from the halogeno-nitrobenzonitriles of general formula (X.2). Reduction of the nitrile function of the intermediates of general formula (X.2), Diagram 3.1, is carried out, for example, in an appropriate solvent such as ether or THF, in the presence of diborane or LAH. The halogeno-nitroanilines/amines (X.3) formed are then protected in the form of Boc (X.4) or of other protective groups (Gp) known to a person skilled in the art then the compounds of general formula (X.4) are subjected to a nucleophilic substitution by a heterocyclic group (het) in a solvent such as DMSO or DMF, in the presence of a base such as $K_2CO_3$, KOH or NaOH, in order to produce the intermediates of general formula (X).

Alternatively, the compounds of general formula (X) as defined previously can be prepared according to a method based on that shown in Diagram 3.2 hereafter:

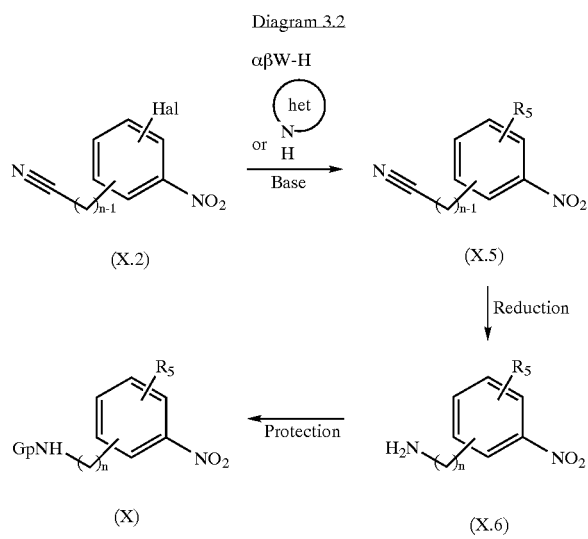

The compounds of general formula (X), Diagram 3.2, in which $R_5$ represents a heterocycle with 5 to 6 members comprising a nitrogen atom (het) or a group comprising a heteroatom W (Wαβ as defined previously), are prepared from halogeno-nitrobenzonitriles of general formula (X.2). The compounds of general formula (X.2) are subjected to a nucleophilic substitution by the appropriate reagent in a solvent such as DMSO or DMF, in the presence of a base such as $K_2CO_3$, KOH or NaOH, in order to produce intermediates of general formula (X.5).

The reduction of the nitrile function of the intermediates of general formula (X.5), Diagram 3.2, is carried out, for example, in an appropriate solvent such as ether or THF, in the presence of diborane or LAH. The halogeno-nitroanilines/amines (X.6) formed are then protected in the form of Boc or other protective groups (Gp) known to a person skilled in the art in order finally to produce intermediates of general formula (X), Diagram 3.2.

The following examples are presented to illustrate the above procedures and must in no case be considered as a limit to the scope of the invention.

EXAMPLES

Example 1

N-{4-[[(2-thienyl)(imino)methyl]amino]phenyl}-1,2-dithiolane-3-pentanamide hydrochloride 1.1) N-{4-[(1,1-dimethylethoxy)carbonylamino]phenyl}-1,2-dithiolane-3-pentanamide 1.84 g (8.81 mmol) of N-BOC-1,4-phenylene diamine, 1.6 ml of triethylamine, 1.7 g (12.6 mmol) of hydroxybenzotrazole, 4.82 g (25.2 mmol) of 1-(3-dimethylaminopropyl-3-ethyl-carbodiimide hydrochloride and 1.6 ml of triethylamine are added successively to a solution of 2 g (9.694 mmol) of (DL)-thioctic acid in 40 ml of dichloromethane. After having agitated the reaction mixture overnight at 25° C., the mixture is diluted with 100 ml of water and agitation is maintained for another 30 minutes. The product is extracted using 3 times 100 ml of dichloromethane. The organic solution is dried over magnesium sulphate, filtered and concentrated under vacuum. The reddish brown powder obtained is suspended in ether (100 ml), filtered and rinsed with the same volume of ether in order to produce a salmon pink powder with a yield of 80.5%. Melting point: 190–195° C.

NMR $^1$H (DMSO d6, 400 MHz, δ): 1.39 (m, 2H, $CH_2$); 1.57 (s, 9H, BOC); 1.61 (m, 4H, $CH_2$); 1.88 (m, 1H, $CH_2$); 2.27 (m, 2H, $CH_2$); 2.50 (m, 1H, $CH_2$); 3.15 (m, 2H, $CH_2$); 3.63 (m, 1H, —S—CH—); 7.34 (d, 2H, arom., J=8.70 Hz); 7.45 (d, 2H, arom., J=9.00 Hz); 9.24 (s, 1H, CONH); 9.77 (s, 1H, CONH-BOC).

1.2) N-(4-aminophenyl)-1,2-dithiolane-3-pentanamide

A stream of HCl gas is passed bubble by bubble at 0° C. into a solution of intermediate 1.1 (6.5 g; 16.4 mmol) in a mixture (200 ml) of ether/ethanol/acetone/dichloromethane (1/1/1/1). The temperature is allowed to rise to ambient overnight. A stream of argon is passed through the reaction mass and the solvents are evaporated to dryness. The evaporation residue is then poured into 100 ml of a cold saturated solution of $NaHCO_3$ and extraction is carried out with 3×100 ml of dichloromethane. The organic phase is dried over magnesium sulphate, filtered and concentrated under vacuum. Then purification is carried out on a silica column (eluent=heptane with 50% ethyl acetate then dichloromethane with 5% ethanol) in order to produce a beige solid with a yield of 29%. Melting point: 55–60° C.

NMR $^1$H (DMSO d6, 400 MHz, δ): 1.38 (m, 2H, $CH_2$); 1.57 (m, 4H, $CH_2$); 1.87 (m, 1H, $CH_2$); 2.22 (m, 2H, $CH_2$); 2.40 (m, 1H, $CH_2$); 3.18 (m, 2H, $CH_2$); 3.62 (m, 1H, —S—CH—); 4.78 (s, 2H, $NH_2$); 6.48 (d, 2H, arom., J=8.64 Hz); 7.20 (d, 2H, arom., J=8.64 Hz); 9.39 (s, 1H, CONH).

1.3) N-{4-[[(2-thienyl)(imino)methyl]amino]phenyl}-1,2-dithiolane-3-pentanamide hydrochloride:

Intermediate 1.2 (0.703 g; 2.37 mmol) is dissolved in 2-propanol (15 ml) and 1.014 g of S-methyl-2-thiophene thiocarboximide hydroiodide (3.56 mmol) (Ann. Chim. (1962), 7, 303–337) is added. After heating at 60° C. for 15 hours, the reaction mixture is concentrated to dryness under vacuum. The residue is taken up in dichloromethane and a saturated aqueous solution of $NaHCO_3$. After decanting, the organic phase is washed successively with 50 ml of a saturated solution of $NaHCO_3$, with water and with salt water. The organic solution is dried over magnesium sulphate, filtered and evaporated under reduced pressure. Then the free base is dissolved in 30 ml of dichloromethane and the solution is cooled down using an ice bath before the dropwise addition of 6.3 ml of a 1N HCl solution in anhydrous ethyl ether. After agitation for 15 hours at 25° C., the crystals obtained are filtered and rinsed with diethyl ether in order to obtain after drying 1.6 g of a light beige solid product with a yield of 77%. Melting point: 258.7–258.9° C.

NMR $^1$H (DMSO d6, 400 MHz, δ): 1.43 (m, 2H, $CH_2$); 1.62 (m, 4H, $CH_2$); 1.88 (m, 1H, $CH_2$); 2.38 (m, 3H, $CH_2$); 3.18 (m, 2H, $CH_2$); 3.63 (m, 1H, —S—CH—); 7.20–8.20 (m, 7H, arom.); 8.79 (broad s, 1H, $NH^+$); 9.78 (broad s, 1H, $NH^+$); 10.36 (s, 1H, CONH) 11.49 (broad s, 1H, $NH^+$). IR: $v_{C=N}$ (amidine): 1580 $cm^{-1}$; $v_{C=O}$ (amide): 1659 $cm^{-1}$.

Example 2

N-{2-{4[[(2-thienyl)(imino)methyl]amino]phenyl}ethyl}-1,2-dithiolane-3-pentanamide 2.A. Method According to the First Approach:

The experimental protocol used is the same as that described for compound 1. Yellow solid. Melting point: 146–148° C.

NMR $^1$H (DMSO d6, 400 MHz, δ): 1.32 (m, 2H, $CH_2$); 1.60 (m, 4H, $CH_2$); 1.88 (m, 1H, $CH_2$); 2.07 (t, 2H, $CH_2$, J=7.36 Hz); 2.41 (m, 1H, $CH_2$); 2.65 (m, 2H, $CH_2$); 3.10–3.30 (m, 4H, $CH_2$); 3.60 (m, 1H, —S—CH—); 6.33 (broad s, 2H, $NH_2$ amidine); 6.78 (d, 2H, arom., J=8.04 Hz); 7.08 (m, 1H, thiophene); 7.12 (d, 2H, arom., J=8.16 Hz); 7.60–7.80 (m, 2H, thiophene); 7.81 (t, 1H, CONH J=5.56 Hz). IR: $v_{C=N}$ (amidine): 1590 $cm^{-1}$; $v_{C=O}$ (amide): 1629 $cm^{-1}$.

2.B. Method According to the Second Approach:

Alternatively, the synthesis of a compound of Example 2 can be carried out according to the method illustrated in Diagrams 3 (with Gp=Boc and $R_3$=2-hydroxy-4,6-dimethoxybenzyl) and 6.

2.B.1) 3,5-dimethoxy-2-({[2-(4-nitrophenyl)ethyl]amino}methyl)phenol:

In a flask containing 200 ml of anhydrous MeOH, the following are added successively under an inert atmosphere: 9.0 g (49.4 mmol) of 4,6-dimethoxysalicaldehyde, 11.6 g (54.3 mmol) of 4-nitrophenethylamine hydrochloride and 7.5 ml of triethylamine. The reaction mixture is agitated vigorously for 15 hours before the addition, by portions, of 2.1 g (55.5 mmol) of $NaBH_4$. Agitation is maintained for another 10 hours before adding 10 ml of water. After a quarter of an hour, the reaction mixture is extracted with twice 100 ml of $CH_2Cl_2$. The organic phase is washed successively with 50 ml of water and with 50 ml of salt water, dried over sodium sulphate, filtered and concentrated under vacuum. The residue is then purified on a silica column (eluent: $CH_2Cl_2$/EtOH: 20/1). An orange oil is obtained with a yield of 58%.

2.B.2) tert-butyl 2-hydroxy-4,6-dimethoxybenzyl[2-(4-nitrophenyl)ethyl]carbamate:

The experimental protocol used is the same as that described for intermediate 7.B.1, intermediate 2.B.1 replacing the p-nitrobenzylamine. A white solid is obtained with a yield of 60%. Melting point: 133.5–134.4° C.

2.B.3) tert-butyl 2-(4-aminophenyl)ethyl(2-hydroxy-4,6-dimethoxybenzyl)carbamate:

The experimental protocol used is the same as that described for intermediate 7.B.2, intermediate 2.B.2 replacing intermediate 7.1. A light yellow oil is obtained with a yield of 90%.

2.B.4) tert-butyl 2-(4-{[(amino(2-thienyl)methylidene]amino}phenyl)ethylcarbamate:

The experimental protocol used is the same as that described for intermediate 1.3, intermediate 2.B.3 replacing intermediate 1.2. These conditions give rise to the N-debenzylation in order to produce the mono protected primary amine with the Boc group. A yellow solid is obtained with a yield of 79%. Melting point: 144° C.

2.B.5) N'-[4-(2-aminoethyl)phenyl]-2-thiophenecarboximidamide:

The experimental protocol used is the same as that described for intermediate 1.2, intermediate 2.B.4 replacing intermediate 1.1. A white solid is obtained with a yield of 79%. Melting point: 169.2–170.5° C.

2.B.6) N-{2-{4[[(2-thienyl)(imino)methyl]amino]phenyl}ethyl}-1,2-dithiolane-3-pentanamide:

The experimental protocol used is the same as that described for intermediate 1.1, intermediate 2.B.5 replacing N-BOC-1,4-phenylene diamine. A yellow solid is obtained with a yield of 79%. Melting point: 146–148° C.

NMR $^1$H (DMSO d6, 400 MHz, δ): 1.32 (m, 2H, $CH_2$); 1.60 (m, 4H, $CH_2$); 1.88 (m, 1H, $CH_2$); 2.07 (t, 2H, $CH_2$, J=7.36 Hz); 2.41 (m, 1H, $CH_2$); 2.65 (m, 2H, $CH_2$); 3.10–3.30 (m, 4H, $CH_2$); 3.60 (m, 1H, —S—CH—); 6.33 (broad s, 2H, $NH_2$ amidine); 6.78 (d, 2H, arom., J=8.04 Hz); 7.08: (m, 1H, thiophene); 7.12 (d, 2H, arom., J=8.16 Hz); 7.60–7.80 (m, 2H, thiophene); 7.81 (t, 1H, CONH J=5.56 Hz). IR: $v_{C=N}$ (amidine): 1590 $cm^{-1}$; $v_{C=O}$ (amide): 1629 $cm^{-1}$.

2.C. Another Method According to the Second Approach:

Another synthesis illustrated in Diagram 3 can also be used, with Gp=Boc. The experimental protocol is, in this case, similar to that described in procedure 7.B hereafter, 4-nitrophenethylamine replacing p-nitrobenzylamine.

Example 3

N-{2-{4[[(2-thienyl)(imino)methyl]amino]phenyl}ethyl}-1,2-dithiolane-3-acetamide hydrochloride 3.A. Method According to the First Approach:

The experimental protocol used is the same as that described for compound 1, with trisnorlipoic acid [2-(1,2-dithiolan-3-yl)acetic acid] (prepared according to *Tetrahedron Letters*, (1997), 38, 33, 5785) replacing lipoic acid. Yellow solid.

NMR $^1$H (DMSO d6, 400 MHz, δ): 1.91 (m, 1H, $CH_2$); 2.30–2.60 (m, 3H, $CH_2$); 2.70–2.90 (m, 2H, $CH_2$); 3.17 (m, 2H, $CH_2$); 3.40 (m, 2H, $CH_2$); 3.93 (m, 1H, —S—CH—); 7.30–7.50 (m, 5H, arom.); 8.10–8.30 (m, 3H, arom. +CONH); 8.86 (broad s, 1H, $NH^+$); 9.80 (broad s, 1H, $NH^+$); 11.50 (broad s, 1H, $NH^+$). MS: MH+=392.1.

3.B. Method According to the Second Approach:

Alternatively, the synthesis of a compound of Example 3 can be carried out according to the method illustrated in Diagrams 3 (with Gp=Boc and $R_3$=2-hydroxy-4,6-dimethoxybenzyl) and 6. The experimental protocol used is the same as that described in procedure 2.B, with trisnorlipoic acid [2-(1,2-dithiolan-3-yl)acetic acid] (prepared according to *Tetrahedron Letters*, (1997), 38, 33, 5785) replacing lipoic acid. Yellow solid.

3.C Another Method According to the Second Approach:

Another synthesis illustrated in Diagram 3 can also be used, with Gp=Boc. The experimental protocol is, in this case, similar to that described in procedure 7.B hereafter, nitrophenethylamine replacing p-nitrobenzylamine and trisnorlipoic acid [2-(1,2-dithiolan-3-yl)acetic acid] (prepared according to *Tetrahedron Letters*, (1997), 38; 33, 5785) replacing lipoic acid.

Example 4

N-[4-(6-amino-4-methyl-2-pyridinyl)butyl]-1,2-dithiolane-3-pentanamide 4.1) 6-(2,5-dimethyl-1H-pyrrol-1-yl)-4-methyl-2-pyridinebutanamine 1 g (5 mmol) of 2-(2,5-dimethyl-1H-pyrrol-1-yl)-4,6-dimethylpyridine (prepared from the 6-amino-2,4-lutidine according to *J. Chem. Soc., Perkin Trans.,* 1984, 12, 2801) is dissolved, under an argon atmosphere, in 10 ml of anhydrous ethyl ether and 1.132 ml (7.5 mmol) of N,N,N,N-tetramethylethylenediamine (TMEDA). The reaction mixture is cooled down to −20° C. and 2.4 ml (6 mmol) of a 2.5 M solution of BuLi in hexane is added dropwise. After 5 hours at −20° C., the reaction mixture is cooled down to −45° C. and 1.68 g (6 mmol) of 1-(3-bromopropyl)-2,2,5,5-tetramethyl-1-aza-2,5-disilacyclopentane is added and the temperature is allowed to return to ambient temperature overnight. 50 ml of a saturated solution of ammonium chloride is added and the mixture is agitated for 2 hours at 25° C. The organic phase is decanted and washed successively with 40 ml of water and 40 ml of salt water, dried over magnesium sulphate, filtered and concentrated under vacuum. The residue obtained is purified on a silica column (eluent=dichloromethane with 5% ethanol) in order to produce a yellow oil with a yield of 62%.

NMR $^1$H (CDCl$_3$, 400 MHz, δ): 1.52 (m, 2H, CH$_2$); 1.78 (m, 2H, CH$_2$); 2.11 (s, 6H, 2×CH$_3$ pyrrole); 2.39 (s, 3H, CH$_3$ pyridine); 2.72 (t, 2H, CH$_2$ J=7.02 Hz); 2.79 (t, 2H, CH$_2$ J=7.62 Hz); 5.87 (s, 2H, pyrrole); 6.85 (s, 1H, pyridine); 6.98 (s, 1H, pyridine).

4.2) N-{4-[6-(2,5-dimethyl-1H-pyrrol-1-yl)-4-methyl-2-pyridinyl]butyl}-1,2-dithiolane-3-pentanamide The experimental protocol used is the same as that described for intermediate 1.1, intermediate 4.1 replacing N-BOC-1,4-phenylenediamine. A yellow oil is obtained.

NMR $^1$H (CDCl$_3$, 400 MHz, δ): 1.30–2.00 (m, 11H, CH$_2$); 2.07 (m, 2H, CH$_2$); 2.11 (s, 6H, 2×CH$_3$ pyrrole); 2.40 (s, 3H, CH$_3$ pyridine); 2.45 (m, 1H, CH$_2$); 2.82 (m, 2H, CH$_2$); 3.10–3.30 (m, 4H, CH$_2$); 3.57 (m, 1H, —S—CH—); 5.87 (s, 2H, pyrrole); 5.94 (broad s, 1H, CONH); 6.87 (s, 1H, pyridine); 6.99 (s, 1H, pyridine). MS: MH+=446.2

4.3) N-[4-(6-amino-4-methyl-2-pyridinyl)butyl]-1,2-dithiolane-3-pentanamide

Intermediate 4.2 (1.53 g; 3.43 mmoles) is dissolved in 55 ml of ethanol with 18 ml of water added to it and 1.2 g (17.2 mmoles) of hydroxylamine hydrochloride is added. The reaction mixture is heated at reflux for 24 hours. After returning to 25° C., the mixture is diluted with 20 ml of a saturated solution of sodium bicarbonate and the product is extracted with 100 ml of-dichloromethane. After decanting, the organic solution is washed successively with 40 ml of a saturated solution of sodium bicarbonate and 40 ml of salt water, dried over magnesium sulphate, filtered and concentrated under vacuum. The evaporation residue is purified on a silica column (eluent=dichloromethane with 2.5% ethanol) in order to produce a yellow oil with a yield of 76%.

NMR $^1$H (CDCl$_3$, 400 MHz, δ): 1.30–1.80 (m, 10H, CH$_2$); 1.89 (m, 1H, CH$_2$); 2.16 (m, 2H, CH$_2$); 2.19 (s, 3H, CH$_3$ pyridine); 2.40 (m, 1H, CH$_2$); 2.58 (m, 2H, CH$_2$); 3.05–3.30 (m, 4H, CH$_2$); 3.56 (m, 1H, —S—CH—); 4.35 (broad s, 2H, NH$_2$); 5.80 (broad s, 1H, CONH); 6.17 (s, 1H, pyridine); 6.35 (s, 1H, pyridine). IR: $v_{C=O}$ (amide): 1637 cm$^{-1}$.

Example 5

N-[4-(6-amino-4-methyl-2-pyridinyl)butyl]-1,2-dithiolane-3-acetamide fumarate The experimental protocol used is the same as that described for compound 4, with trisnorlipoic acid [or 2-(1,2-dithiolan-3-yl)acetic acid] (prepare according to *Tetrahedron Letters,* 1997, 38, 33, 5785) replacing lipoic acid. The free base is then salified using fumaric acid in a solvent mixture of acetone/methyl ethyl ketone (50/50). The fumarate is obtained in the form of a cream powder with a yield of 14.8%.

NMR $^1$H (DMSO d6, 400 MHz, δ): 1.40 (m, 2H, CH$_2$); 1.57 (m, 2H, CH$_2$); 1.92 (m, 1H, CH$_2$); 2.15 (s, 3H, CH$_3$ pyridine); 2.30–2.70 (m, 5H, CH$_2$); 3.03–3.18 (m, 4H, CH$_2$); 3.94 (m, 1H, —S—CH—); 6.17 (s, 1H, pyridine); 6.26 (s, 1H, pyridine); 6.00–6.60 (broad s, 2H, —CO$_2$H fumaric acid); 6.60 (s, 2H, CH═CH, fumaric acid); 7.90 (broad s, 1H, CONH). IR: $v_{C=O}$ (amide): 1649 cm$^{-1}$. MS: MH+=326.2

Example 6

N-(4-{[amino(2-thienyl)methylidene]amino}phenyl)-2-(1,2-dithiolan-3-yl)acetamide The experimental protocol used is the same as that described for compound 1, with trisnorlipoic acid [or 2-(1,2-dithiolan-3-yl)acetic acid] (prepared according to *Tetrahedron Letters,* (1997), 38, 33, 5785) replacing lipoic acid. Yellow foam.

NMR $^1$H (DMSO d6, 400 MHz, δ): 2.00 (m, 1H, CH$_2$); 2.40–2.80 (m, 3H, CH$_2$); 3.00–3.30(m, 2H, CH$_2$); 4.10(m, 1H,)—S—CH—); 6.50–6.80 (broad s, 2H, NH$^+$); 6.80–7.10 (m, 3H, arom.); 7.50–7.80 (m, 4H, arom.); 9.93 (s, 1H, CONH). MH+=364.1.

Example 7

N-(4-{[amino(2-thienyl)methylidene]amino}benzyl)-5-(1,2-dithiolan-3-yl)pentanamide 7.A. Method According to the First Approach:

The experimental protocol used is the same as that described for compound 1, tert-butyl 4-(aminomethyl)phenylcarbamate replacing N-BOC-1,4-phenylene diamine. White solid. Melting point: 151.9–152.1° C.

7.B. Method According to the Second Approach:

7.B.1. tert-butyl 4-nitrobenylcarbamate:

5.66 g (30.0 mmol) of p-nitrobenzylamine hydrochloride is dissolved in a mixture of 100 ml of dichloromethane and 9.2 ml of triethylamine. The mixture is cooled down using an ice bath before the addition in several portions of 7.2 g (33.0 mmol) of (Boc)$_2$O. The reaction mixture is agitated at 23° C. for 12 hours and poured into a water-ice mixture. The organic phase is decanted, washed successively with 20 ml of water and with 20 ml of salt water. After drying over sodium sulphate, filtration and concentration under vacuum, and trituration with isopropyl ether a white solid is obtained with a yield of 67.4%. Melting point: 107.8° C.

7.B.2. tert-butyl 4-aminobenzylcarbamate:

A solution of intermediate 7.B.1 (5.1 g; 20.2 mmol) in 66 ml of a dichloromethane, ethyl acetate and THF mixture (1 ml/60 ml/5 ml) as well as 1.0 g of 10% Pd/C is introduced into a stainless steel autoclave equipped with a magnetic stirrer. The reaction mixture is agitated under hydrogen pressure (1.5 bar) at a temperature of 20° C. for 12 hours. The Pd/C is then eliminated by filtration and the filtrate is concentrated under vacuum. Once the evaporation residue is purified by trituration with isopropyl ether, a white grey powder is obtained with a yield of 42%. Melting point: 74.4° C.

7.B.3. tert-butyl 4-{[amino(2-thienyl)methylidene]amino}benzylcarbamate:

The experimental protocol used is the same as that described for intermediate 1.3, intermediate 7.B.2 replacing intermediate 1.2. An orange oil is obtained with a yield of 99%.

NMR $^1$H (DMSO d6, 400 MHz, δ): 1.40 (s, 9H, 3×CH$_3$); 4.19 (d, 2H; CH$_2$, J=6.00 Hz); 7.30–7.40 (m, 5H, arom.); 7.46 (t, 1H, CONH , J=6.00 Hz); 8.10–8.20 (m, 2H, thiophene); 9.00–10.00 (broad s, 2H, NH$_2$ amidine); 11.10–11.40 (broad s, 1H, HI). MH+=332.2.

7.B.4. N'-[4-(aminomethyl)phenyl]-2-thiophenecarboximidamide:

The experimental protocol used is the same as that described for intermediate 1.2, intermediate 7.B.3 replacing intermediate 1.1. A white solid is obtained with a yield of 92%. Melting point: 241.1–241.6° C.

7.B.5. N-(4-{[amino(2-thienyl)methylidene]amino}benzyl)-5-(1,2-dithiolan-3-yl)pentanamide:

The experimental protocol used is the same as that described for intermediate 1.1, intermediate 7.B.4, replacing N-BOC-1,4-phenylene diamine. A white solid is obtained with a yield of 40%. Melting point: 151.9–152.1° C.

Example 8

N-(5-{[amino(2-thienyl)methylidene]amino}-2-methoxyphenyl)-5-(1,2-dithiolan-3-yl)pentanamide (Prepared Using a Method According to the First Approach)

8.1. 5-(1,2-dithiolan-3-yl)-N-(2-methoxy-5-nitrophenyl)pentanamide:

3.36 g (21.0 mmol) of 2-methoxy-5-nitroaniline, triethylamine (6.0 ml), 3.0 g (22.0 mmol) of hydroxybenzotriazole and 4.21 g (22.0 mmol) of 1-(3-dimethylaminopropyl)-3-ethyl-carbodiimide hydrochloride are added successively to a solution of 4.12 g (21.0 mmol) of (DL)-thioctic acid in 50 ml of DMF. The reaction mixture is agitated for 18 hours at 80° C., then diluted with 400 ml of water and agitation is maintained for a further 30 minutes. The product is extracted using 3 times 200 ml of dichloromethane. The organic solution is dried over magnesium sulphate, filtered and concentrated under vacuum. The solid obtained is filtered and rinsed with diethyl ether in order to obtain after drying 2.6 g of a solid yellow product (yield 37%.). Melting point: 116.7–117.1° C.

8.2. N-(5-amino-2-methoxyphenyl)-5-(1,2-dithiolan-3-yl)pentanamide:

10 ml of a saturated aqueous solution of ammonium chloride and 12.0 g (0.183 mol) of Indium in powder form are added successively to a solution of 2.6 g (13.20 mmol) of intermediate 8.1 in 40 ml of ethanol,. The reaction medium is then heated at reflux for 4.5 hours (*Synlett* (1998), 9, 1028). The mixture is cooled down to ambient temperature and filtered on celite. The filtrate is alkalinized to pH 10 with a 50% solution of sodium hydroxide. The reduced product is extracted using 4 times 150 ml of dichloromethane. The organic solution is dried over magnesium sulphate, filtered and concentrated under vacuum in order to produce a brown oil. The oil is dissolved in 50 ml of ethyl acetate and the mixture is cooled down to 0° C. using an ice bath. A 10% solution of potassium bicarbonate in water is then added dropwise. The reaction mixture is agitated for approximately 10 minutes at 0° C., then iodine solution (0.8 g in 10 ml of ethyl acetate) is added dropwise until the iodine colouring persists. The product is extracted using 4 times 100 ml of ethyl acetate and the organic solution is dried over magnesium sulphate, filtered and concentrated under vacuum. Purification is then carried out on a silica column (eluent=5% ethanol in dichloromethane) in order to produce a brown oil (1.0 g; yield 63%).

MH+=327.20.

8.3. N-(5-{[amino(2-thienyl)methylidene]amino}-2-methoxyphenyl)-5-(1,2-dithiolan-3-yl)pentanamide:

The experimental protocol used is the same as that described for Stage 1.1, intermediate 8.2 replacing the N-BOC-1,4-phenylene diamine. A brown gum is obtained with a yield of 32%.

MH+=436.10.

Example 9

N-[5-{[amino(2-thienyl)methylidene]amino}-2-(dimethylamino)benzyl]-5-(1,2-dithiolan-3-yl)pentanamide (Prepared Using a Method According to the Second Approach)

9.1. 2-(dimethylamino)-5-nitrobenzonitrile:

1.66 g (10.0 mmol) of 2-fluoro-5-nitrobenzonitrile, 1.22 g (15.1 mmol) of dimethylamine hydrochloride and 3.46 g (25.1 mmol) of potassium bicarbonate is dissolved, under an argon atmosphere, in DMF (30 ml) then the reaction medium is heated at a temperature of 80° C. for 18 hours. The reaction mixture is cooled down to 0° C. and ice-cooled water is added. The reaction mixture is extracted with ethyl acetate and the organic phase is washed successively with 50 ml of water and 50 ml of salt water, dried over magnesium sulphate, filtered and concentrated under vacuum. The evaporation residue is purified by trituration with isopropyl ether and the solid obtained is filtered and rinsed with isopentane in order to obtain after drying 2.0 g of a solid yellow product (yield 100%). Melting point: 109–110.5° C.

9.2. 2-(aminomethyl)-N,N-dimethyl-4-nitroaniline:

Intermediate 9.1 (1.5 g; 7.85 mmol) is solubilized under an argon atmosphere in THF (40 ml). A solution of diborane (16 ml, 1M in THF) is added then the reaction medium is heated at reflux for 6 hours. Methanol (30 ml) is added then HCl gas is bubbled through the mixture for 15 minutes. The reaction medium is evaporated to dryness and taken up with a solution of sodium bicarbonate. Extraction is carried out with dichloromethane then the organic phase is washed successively with 50 ml of water and 50 ml of salt water, dried over magnesium sulphate, filtered and concentrated under vacuum. The evaporation residue is purified by crystallization from a mixture of isopropyl ether and dichloromethane in order to produce a solid yellow product with a yield of 82%. Melting point: 196–200° C.

9.3. tert-butyl 2-(dimethylamino)-5-nitrobenzylcarbamate:

The experimental protocol used is the same as that described for Stage 7.B.1 of Example 7, intermediate 9.2 replacing the p-nitrobenzylamine hydrochloride. A yellow solid is obtained with a yield of 100%. Melting point: 101–102° C.

9.4. tert-butyl 5-amino-2-(dimethylamino)benzylcarbamate:

The experimental protocol used is the same as that described for Stage 7.B.2 of Example 7, intermediate 9.3 replacing intermediate 7.B.1. A brown oil is obtained with a yield of 15%.

MH+=266.20.

9.5. tert-butyl 5-{[amino(2-thienyl)methylidene]amino}-2 (dimethylamino)benzyl carbamate The experimental protocol used is the same as that described for Stage 1.3 of Example 1, intermediate 9.4 replacing intermediate 1.2. A yellow solid is obtained with a yield of 64%. Melting point: 175.8° C.–177.0° C.

9.6. N'-[3-(aminomethyl)-4-(dimethylamino)phenyl]-2-thiophenecarboximidamide:

The experimental protocol used is the same as that described for Stage 1.2 of Example 1, intermediate 9.5 replacing intermediate 1.1. A yellow solid is obtained with a yield of 66%. Melting point: 169.0–170.0° C.

9.7. N-[5-{[amino(2-thienyl)methylidene]amino}-2-(dimethylamino)benzyl]-5-(1,2-dithiolan-3-yl)pentanamide:

The experimental protocol used is the same as that described for Stage 1.1 of Example 1, intermediate 9.6 replacing the N-BOC-1,4-phenylenediamine. A white solid is obtained with a yield of 67%. Melting point: 183.5–185.0° C.

Example 10

N-[5-{[amino(2-thienyl)methylidene]amino}-2-(1H-pyrrol-1-yl)benzyl]-5-(1,2-dithiolan-3-yl)pentanamide The experimental protocol used is the same as that described for the compound of Example 9, pyrrole replacing the dimethylamine hydrochloride in the first stage. A white solid is obtained with a yield of 72%. Melting point: 156.1–157.6° C.

Pharmacological Study of the Products of the Invention
Study of the Effects on Neuronal Constitutive NO Synthase of a Rat's Cerebellum The inhibitory activity of the products of the invention is determined by measuring their effects on the conversion by NO synthase of [³H]L-arginine into [³H]L-citrulline according to the modified method of Bredt and Snyder (*Proc. Natl. Acad. Sci. USA,* (1990) 87: 682–685). The cerebellums of Sprague-Dawley rats (300 g—Charles River) are rapidly removed, dissected at 4° C. and homogenized in a volume of extraction buffer (HEPES 50 mM, EDTA 1 mM, pH 7.4, pepstatin A 10 mg/ml, leupeptin 10 mg/ml). The homogenates are then centrifuged at 21000 g for 15 min at 4° C. Dosage is carried out in glass test tubes in which 100 µl of incubation buffer containing 100 mM of HEPES (pH 7.4), 2 mM of EDTA, 2.5 mM of $CaCl_2$, 2 mM of dithiotreitol, 2 mM of reduced NADPH and 10 µg/ml of calmodulin are distributed. 25 µl of a solution containing 100 nM of [³H]L-arginine (specific activity: 56.4 Ci/mmole, Amersham) and 40 µM of non-radioactive L-arginine are added. The reaction is initiated by adding 50 µl of homogenate, the final volume being 200 µl (the missing 25 µl are either water or the tested product). After 15 min, the reaction is stopped with 2 ml of stopping buffer (20 mM of HEPES, pH 5.5, 2 mM of EDTA). After passing the samples through a 1 ml column of DOWEX resin, the radioactivity is quantified by a liquid scintillation spectrometer.

The compounds of examples 1, 2, 3, 4, 5 described above show an $IC_{50}$ lower than 4.5 µM.

Study of the Effects on the Oxidation Stress Induced by Glutamate on Cells in Culture (HT-22).

The inhibitory activity of the products of the invention is determined by measuring their ability to protect the cells of a mouse hippocampal line (HT-22) of an oxidation stress caused by glutamate. The biosynthesis of glutathione, an essential element of cell detoxification of free radicals, requires the active transport of cystine to the interior of the cell. The glutamate by opposing the penetration of cystine causes a reduction in the level of glutathione which leads to the death of the cell due to oxidation stress (Davis, J. B. and Maher, P., *Brain Res.,* (1994) 652: 169–173; Murphy, T. H. et al., *Neuron,* (1989) 2: 1547–1558). The cells are cultured at 37° C. in a DMEM medium with 10% of foetal calf serum added to it. The tests are carried out in 96-well plates containing 5000 cells per well. The glutamate (5 mM) is added to the medium containing or not containing the products to be tested. The cell viability is tested after 24 h by the MTT method (Hansen, M. B. et al., *J Immunol. Methods* (1989), 119, 203–210). The ability of the compounds to protect the cells from the toxic action of the glutamate is estimated in $EC_{50}$, calculated relative to the viability of cells which have not been subjected to the action of glutamate considered as 100% viability.

The compounds of Examples 1, 2, 3, 5 described above show an $EC_{50}$ lower than 30 µM.

What is claimed is:

1. A compound of a formula selected from the group consisting of

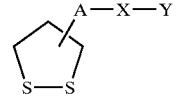

(Ia)

wherein

A is selected from the group consisting of —$(CH_2)_m$—$NR_3CO(CH_2)_n$—, —$(CH_2m)$—$CONR$—$(CH_2)_n$—, —$(CH_2)_m$—$NR_3$—$(CH_2)_n$, —$(CH_2)_m$—$CONR_3$—$(CH_2)_p$—$NR_4$—$(CH_2)_n$—, —$(CH_2)_m$—$NR_3$—$CO$—$NR_4$—$(CH_2)_n$— and —$(CH_2)_m$—, m and n are individually integers from 0 to 6, p being an integer from 2 to 6, and $R_3$ and $R_4$ are individually hydrogen or alkyl of 1 to 6 carbon atoms;

X is

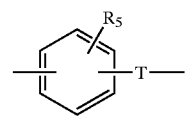

wherein the T group, which is attached to the Y group, is —$(CH_2)i$-, i is 0 and $R_5$ is selected from the group consisting of hydrogen, alkyl of 1 to 6 carbon atoms and —$(CH_2)_m$-Q, Q is selected from the group consisting of halogen, hydroxy, cyano, amino, alkoxy, alkylamino, dialkylamino and a heterocycle with 5 to 6 ring members with the heterocyclic members being selected from the group consisting of —O—, —$N(R_6)$— and —S—, $R_6$ is hydrogen or alkyl of 1 to 6 carbon atoms or the bond to the phenyl ring of X;

and Y is

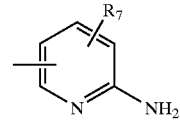

and $R_7$ is hydrogen or alkyl of 1 to 6 carbon atoms and a pharmaceutically acceptable salt thereof.

2. A compound of claim 1, wherein X is

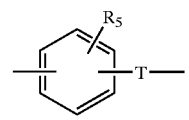

T, which is attached to Y is —$(CH_2)i$-, i is 0, and $R_5$ is selected from the group consisting of pyrrole, imidazole, pyrazole, triazole, thiazolidine, pyrrolidine, piperidine, piperazine, N-alkyl-piperazine, thiomorpholine, morpholine and azetidine.

3. A compound of claim 1 selected from the group consisting of
—N-[4-(6-amino-4-methyl-2-pyridinyl)butyl]-1,2-dithiolane-3-pentanamide; and
—N-[4-(6-amino-4-methyl-2-pyridinyl)butyl]-1,2-dithiolane-3-acetamide; and a pharmaceutically acceptable salt.

4. A process for the preparation of a compound of claim 1 wherein A is —$(CH_2)_m$—$CONR_3$—$(CH_2)_n$—, $R_3$ is hydrogen or alkyl of 1 to 6 carbon atoms, comprising reacting a compound of the formula

$$HN(R_3)—A'—X—Y \qquad (VII)a$$

wherein $R_3$ is as defined above, X and Y are as defined in claim 1 and A' is —$(CH_2)_n$—, n is an integer of 0 to 6, with a compound of the formula

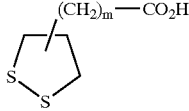

(I.vi)

in which m is an integer from 0 to 6.

5. A process for the preparation of a compound of claim 1 wherein A is —$(CH_2)_m$—$NR_3$—CO—$NR_4$—$(CH_2)_n$ as defined previously, comprising reacting a compound of the formula

$$HN(R_4)—A'—X—Y \qquad (VII)b$$

$R_4$ is as defined above, X and Y are as defined in claim 1 and A' is —$(CH_2)_n$—, n is an integer from 0 to 6, with a compound of the formula

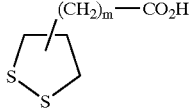

(I.vi)

m is an integer from 0 to 6, and with diphenylphosphorylazide in the presence of a base.

6. A composition for inhibiting NO synthase activity and regeneration of antioxidants comprising an amount of a compound of claim 1 sufficient to inhibit such activity and an inert pharmaceutical carrier.

7. A method of inhibiting both NO synthase activity and regeneration of antioxidants in warm-blooded animals comprising administering to warm-blooded animals in need thereof an amount of a compound of claim 1 sufficient to inhibit said activity.

8. The method of claim 6 wherein the conditions being treated are conditions wherein the nitrogen monoxide and/or the redox status of the thiol groups involved are selected from the group consisting of disorders of the central or peripheral nervous system particularly well represented by Parkinson's disease, cerebrovascular disorders, proliferative and inflammatory diseases, vomiting, septic shock, pathologies resulting from radioactive irradiations, solar radiations or organ transplants, autoimmune and autosomal diseases, cancer and all conditioned by a production or a dysfunction involving nitrogen monoxide and/or involving the redox status of thiol groups.

9. The method of claim 7 wherein the condition being treated is a cardiovascular disorder.

10. The method of claim 9 wherein the cardiovascular disorder is selected from the group consisting of migraine, cerebral infarctions of ischemic or hemorrhagic origin, ischemias and thromboses.

11. The method of claim 7 wherein the condition being treated is a disorder of the control or peripheral nervous system.

12. The method of claim 11 wherein the central or peripheral nervous system disorder is selected from the group consisting of neurodegenerative diseases, pain, cerebral and bone marrow traumas, addition to opiates, alcohol and addictive substances, erective and reproductive disorders, cognitive disorders, encephalopathies, depression, anxiety, schizophrenia, epilepsy, sleep disorders and eating disorders.

* * * * *